United States Patent [19]

Voelter et al.

[11] Patent Number: 4,624,804

[45] Date of Patent: Nov. 25, 1986

[54] PROCESS OF PREPARING RELAXIN FROM MILK

[75] Inventors: Wolfgang Voelter, Tubingen-Hagelloch; Theodor Lippert, Tubingen, both of Fed. Rep. of Germany

[73] Assignee: Serono Pharmazeutische Praparate GmbH, Freiburg, Fed. Rep. of Germany

[21] Appl. No.: 536,760

[22] Filed: Sep. 28, 1983

[30] Foreign Application Priority Data

Sep. 30, 1982 [DE] Fed. Rep. of Germany ....... 3236264

[51] Int. Cl.$^4$ .................... C07K 7/10; A61K 37/24
[52] U.S. Cl. ..................................... 530/366; 424/97; 514/12
[58] Field of Search ............. 260/112 R; 424/97, 177; 514/12

[56] References Cited

U.S. PATENT DOCUMENTS

| | | | |
|---|---|---|---|
| 3,008,878 | 11/1961 | Keck | 424/177 |
| 3,096,246 | 7/1963 | Doczi | 424/97 |
| 3,178,349 | 4/1965 | Ito et al. | 260/112 R |
| 3,962,416 | 6/1976 | Katzen | 424/19 |
| 4,267,101 | 5/1981 | Bigazzi | 260/112 R |
| 4,391,904 | 7/1983 | Litman et al. | 435/7 |

OTHER PUBLICATIONS

*Chemical Abstracts,* 80, 94(1974), Abst. No. 67606x.
*Chemical Abstracts,* 96, 136070(1982), Abst. No. 136066r.
*Chemical Abstracts,* 88, 224(1978), Abst. No. 71076g.
*Chemical Abstracts,* 95, 452(1981), Abst. No. 22224q.
*Chemical Abstracts,* 96, 96(1982), Abst. No. 211088e.

*Primary Examiner*—Delbert R. Phillips
*Assistant Examiner*—F. T. Moezie
*Attorney, Agent, or Firm*—Walter H. Schneider

[57] ABSTRACT

The disclosure relates to a process of preparing relaxin from aqueous, decaseined milk or milk concentrate. Proteins are precipitated and separated, and a relaxin-containing precipitate is produced subsequently. The relaxin-containing precipitate is then purified in the customary manner. There is also disclosed a pharmaceutically active product containing such relaxin.

1 Claim, 1 Drawing Figure

PROCESS OF PREPARING RELAXIN FROM MILK

BACKGROUND OF THE INVENTION

1. Field of the Invention

The present invention relates to a process of preparing relaxin, and more particularly to a process of preparing relaxin of high purity from milk, as well as relaxin prepared in accordance with such processes, and pharmaceutical products containing such relaxin of milk origin.

Relaxin was first described in 1926 by Frederick Hisaw who designated it as a hormone. He discovered the hormone when injecting blood serum, extracted from pregnant rabbits, in guinea-pigs and observing a relaxation of the symphyseal ligament.

The further elucidation of relaxin in subsequent years was rather scarce, and only at the beginning of the seventies did Sherwood and O'Byrne succeed in obtaining relaxin of high purity by column-chromatographical methods. The purification methods of Sherwood et al. [O. D. Sherwood and E. M. O'Byrne: Arch. Biochem. Biophys. 160, 185 (1974)], to this date, are the most frequently employed ones, as well as being the most effective methods for the preparation of relaxin of high purity.

In subsequent developments, relaxin was not only determined in the organs of the genital tract, but also in the blood serum of various species of mammals (homo sapiens, cattle, pig, dog, rat and mouse), primarily during the pregnancy period thereof. The primary locus of production of the hormone is presumably the corpus luteum of the ovary, and relaxin is there prepared together with estrogen, progesterone and androgen. Isolation of relaxin was primarily from the ovaries of pregnant pigs, due to the considerably greater concentration of relaxin in comparison to other The relaxin from pigs and sharks, aside from relaxin from rats, is to date the only of the hormones of the type in which the primary structure is known by sequencing of the isolated peptide. On the other hand, relaxin was not only determined in the females, but also in male mammals (human), as well as in male (chicken) and female non-mammals (shark).

In the human and chicken the relaxin was found in the testes. It is of note, however, that relaxin is not evident in the testicles or blood serum of bears or rats. Relaxin increases the sperm immobility in male species.

The concentration of relaxin increases strongly during the course of pregnancy of the animals. Very frequently an increase in the concentration occurs just prior to giving birth.

It is presumed that the corpus luteum is the primary source of relaxin in women, particularly during pregnancy where it is determinable in the blood. The formation of relaxin is so small in females which are not pregnant that the determination in the blood is hardly possible. The hormone hitherto only presumed in women was recently also determined in human semen or seed plasma.

The content of relaxin-containing substance in human milk and in blood plasma, at various time periods after giving birth, is indicated in the following table.

TABLE

| Number of Patients | Milk pg/ml (Range) | Plasma pg/ml (Range) | Period after Birth |
|---|---|---|---|
| 6 | 193 (n.n.–700) | 82 (n.n.–203) | day 3 |
| 11 | 286 (n.n.–617) | 28 (n.n.–143) | day 4 |
| 11 | 391 (n.n.–790) | 19 (n.n.–150) | day 5 |
| 7 | 438 (n.n.–810) | 32 (n.n.–223) | day 6 |
| 6 | 568 (353–930) | n.n. | 2–4 weeks |
| 8 | 464 (177–741) | n.n. | 5–12 weeks |
| 4 | 495 (229–937) | n.n. | 18–34 weeks | n.n. = not detectable.

It is known that relaxin is produced from corpus luteum during the pregnancy of many animals. For many years it was not known whether the placenta is another rawmaterial source for the production of human relaxin [M. X. Zarrow, E. G. Holmstrom and H. A. Salhanick: J. Clin. Endocr. 15, 22 (1955); F. D. Dallenbach and G. Dallenbach-Hellweg: Virchows Arch. Path. Anat. Physiol. 337, 301 (1964) and G. Weiss, E. M. O'Byrne and B. C. Steinetz: Science 194, 948 (1970)]. It is now appears that the human decidua contains relaxin [M. Bigazzi, F. Nardi, P. Bruni and G. Petrucci: J. Clin. Endocrinol. Metab. 51, 939 (1980); S. Yamamoto, S. C. M. Kwok, F. C. Greenwood and G. D. Bryant-Greenwood: J. Clin. Endocrinol. Metab. 52, 601 (1981); S. Krassnigg, H. K. Rjosk, G. K. Stalla and K. von Werden: Acta Endocrinol. Suppl. 246, 99 (1982)].

More recent investigations have shown that physiological effects are attributable to relaxin, particularly human relaxin, and, accordingly, it is nowadays of considerable clinical interest.

Relaxin exhibits effects on the uterus, for example, it affects the uterus motility and causes a softening of the cervix. In vitro and in vivo investigations of uteri of rats and mice have shown a prevention of spontaneous contractions of the myometrium through relaxin. Many biochemical changes occurring in the cervix are induced by relaxin. This is the case in the intake of water, glycogen, the depolymerization of the base-substance, and the activation of the collagen-peptidase.

Relaxin, furthermore, shows effects on the vaginal epithelium, since it brings about hardening, and shows an effect on the growth of breast glands. Relaxin acts synergistically with progesteron and estrogen and produces an increase of the lubulo-alveolar tissue. It furthermore causes dilation of the symphyseal ligament.

Distinctions are made between relaxins of different origins, i.e. from pigs, cattle, rats, depending wherefrom the respective substance was won. The different relaxins are all polypeptide hormones which vary, in part and in minor aspects, in their amino acid sequence, the molecular weight, and their relaxin activity.

However, two peptide chains are common in relaxin, which chains are joined by two cystin radicals. Furthermore, all relaxins show similar pharmacological effects.

2. Description of the Prior Art

A process for the extraction and purification of relaxin from ovaries of pregnant animals has been described in U.S. Pat. No. 2,952,431. A process of preparing human relaxin from foetus-membranes is described in DE-OS No. 3,102,487 (DE-OS=German Layed Open Patent Publication). These known processes, however, entail the disadvantage that starting materials are used which are difficult to obtain and are, furthermore, available only in limited quantity. Furthermore, the isolation and purification includes many steps and, accordingly, such known processes are labor-intensive and very expensive. The report "Investigations of Purification, Determination and Effects of Relaxin (Untersuchungen über Reinigung, Bestimmung und Wirkung des Relaxin)," by H. Struck, Forschungsberichte des Landes Nordrheinwestfalen (Research Reports of the State of North-Rhine-Westfalia) No. 2304, provides details for purification of relaxin, its determination, and its effects.

Further details in purification and determination, or identification, of relaxin may be had from the recently published summary, Gillian D. Bryant-Greenwood: *Endocrine Reviews,* Vol. 3, No. 1, 1982, p. 62, as well as the references cited therein. This summary and the references mentioned therein are expressis verbis referenced herein.

A new purification process for relaxin, including among others, gel-permeation and ion-exchange chromatography, has also recently been described, M. J. Fields et al.: *Annals of the New York Academy of Sciences,* Vol. 380, 1982, p. 36 ff.

To-date, however, there was a lack of opportunities to recover relaxin in larger quantities and in a simple manner. As indicated in the foregoing, the starting materials for isolating relaxin are relatively scarce and,. accordingly, relaxin is accessible only to a very limited extent. The full synthesis of relaxin could not be achieved and it can be presumed that relaxin prepared synthetically would be rather expensive.

The known methods of preparing relaxin yield a product having pharmacological effects which vary in conformity with the particular method of preparing, as well as being subject to the properties or effects of the starting material for preparing relaxin. This gives rise to the assumption that relaxin identified and obtained in accordance with the known methods is not of constant uniformity, and moreover also contains impurities which could not be eliminated in the past.

SUMMARY OF THE INVENTION

In view of the physiological properties of relaxin there remains the need for simple processes which yield relaxin in adequate quantities and, accordingly, it is one object of the present invention to provide a method of preparing relaxin which method allows isolating and winning of relaxin from inexpensive and easily accessible starting materials, especially from milk.

It is also an object of the present invention to provide relaxin of milk origin as a product which has constant properties and which particularly during the respective analyses exhibits the same reactions, as well as having constant pharmacological properties and effects.

It is further an object of the invention to provide relaxin of milk origin as a product having properties which are independent of the production methods used, as well as being independent of the starting material.

It is also an object of the present invention to provide a process of preparing relaxin from milk origin of very high purity.

In accordance with the present invention there is provided a process of recovering relaxin, which includes the steps of (1) cooling an aqueous, decaseined milk, a milk concentrate or an aqueous solution of milk powder, to a temperature in the range above the freezing temperature or point up to 15° C., as required filtering, (2) adding to the cooled fluid the 0.5 to 5-fold volume of a water-soluble, organic solvent, for the precipitation of the proteins, (3) separating the resulting precipitate at a temperature in the range above the freezing temperature up to 15° C., (4) adding to the obtained fluid the 1 to 10-fold volume of a water-soluble, organic solvent which has a temperature in the range of from −10° C. to −70° C., whereby the solvent can be the same or some other as that in step 2, (5) retaining the reaction mixture 0 to 24 hours at a temperature in the range of from above the freezing temperature of the reaction mixture to +15° C., and (6) separating the relaxin-containing precipitate.

The present invention is also concerned with a process for the purification of the relaxin, which includes: (7) suspending the precipitate obtained in step 6 in the 0.5 to 5-fold volume of an aqueous buffer solution having a pH value in the range of from 4.8 to 6.0, or in distilled water, and filtering, as required, (8) as required, adding 0.1 to 0.5% sodium azide, as required, 0.05 to 5 mM phenyl methane sulfonyl fluoride, or chloride, to the resulting solution, (9) as required, concentrating the solution, (10) filtering the reaction mixture, or the relaxin-containing fractions, respectively, by means of an ultra-membrane-filter having an exclusion limit of 10 000 Daltons, and/or (11) subjecting the reaction mixture, or the relaxin-containing fractions, respectively, to an ion-exchange chromatography, (12) subjecting the reaction mixture, or the relaxin-containing fractions, respectively, to a gel filtration, whereby the steps 10, 11 and 12 can be carried out in any desired sequence and several times, as desired, and whereby the step 12 is necessary and at least one of the steps 10 or 11 must be carried out; and (13) concentrating the fractions containing the relaxin, and recovering the purified relaxin.

In accordance with a further aspect of the invention there is also provided a process for the production of relaxin of high purity from milk, wherein a solution of purified relaxin is subjected to a high-purification step including carrying out: (14) reversed-phase chromatography, or/and (15) HPLC ion-exchange chromatography, or/and (16) HPLC gel chromatography, or/and (17) a batch process by means of ion-exchange chromatography with subsequent eluting, and (18) as required, one of gel chromatography or chromato-focussing and comprising: (19) concentrating the fraction containing the relaxin, and recovering the high-purity relaxin, whereby the steps 14 to 17, as required, can be repeated as desired and whereby at least two of the steps 14 to 17 must be carried out.

The invention is also concerned with the relaxin-containing fraction obtained in accordance with the invention and with highly pure relaxin obtained by the purification and ultra- or super-purification in accordance with this invention. In accordance with another aspect of the invention there is provided a pharmaceutical product which includes relaxin, aside from the usual carrier substances and diluents; or including a relaxin-containing fraction obtained in accordance with the teachings of this invention, in addition to the usual addition and carrier substances.

It was surprising and not obvious that relaxin is present in milk of mammals, particularly normal milk from cows, and that it can be isolated in a simple manner from such milk.

The starting materials for the process of the invention include mammalian milk, such as milk of cows, pigs, mares, goats and sheep. Milk of cows is preferred since such milk is available in large quantities. As well, milk concentrate may be used, i.e. concentrated forms of the types of milk listed in the foregoing, obtained, for example, by concentration techniques such as distillation, lyophilizing and the like. Furthermore, milk powder dissolved or suspended in water to provide as starting material milk solutions, suspensions and concentrates are also within the scope of this invention. Milk powder is often available in large quantities, and it was surprisingly found that relaxin is contained in milk powder without changes.

In the processing according to the present invention casein has to be removed from the milk or milk concentrate. This is carried out by methods which are known per se. It was surprising, and not obvious, that relaxin would not be removed together with the casein, the latter being a protein, from milk, but that the relaxin is retained in the fluid of in the solution at hand. It was to be expected that relaxin, being present as indicated above only small quantities in the milk, would be removed together with casein from the milk.

In accordance with one aspect of the invention the aqueous solution of decaseined milk, or milk concentrate, is cooled to a temperature in the range of from a temperature above the pertaining freezing point to about +15° C., preferably to a temperature in the range of from about +1° to about +10° C., and particularly preferred is a range of from +2° C. to +6° C. Cooling may be carried out continuously or discontinuously. For example, the milk may be passed through a helical reactor where being cooled.

For the precipitation of the contained proteins there is next added a water-miscible solvent, in an amount of from about 0.5 to about 5 times the pertaining volume. Preferred is a range of from about 1 to 3 times the pertaining volume. The amount will be in conformity with the presence of either milk or milk concentrate. The amount can readily be determined by a man skilled in the art. Addition of the solvent can also be continuously or discontinuously. Precipitated proteins are separated by known procedures, e.g. filtration, centrifuging, settling and the like. Next there is added to the resulting fluid or solution the 1 to 10-fold volume of a water-soluble, organic solvent which has been cooled to a temperature in the range of from about −10° to −70° C., preferably to a range of from −10° to −65° C. It is also preferred to use the 2 to 7-fold volume. The solvent may be the same, or another, as used in the protein precipitation-step. The solvents may include solvents which are at least 10% water-soluble, and examples include alcohols such as methanol, ethanol, isopropanol, n-propanol, ketones such as acetone, diethyl ketone, methyethyl ketone, and ethers such as diethyl ether and dioxane.

This step provides a precipitate which can be separated immediately. On the other hand, it may be left for a period of time up to about 20 hours and at a temperature in the range of from the pertaining freezing point of the reaction mixture to about +15° C. This is recommended in those instances where precipitation is not complete. It may be advantageous to stir the reaction mixture, although such a step is not absolutely necessary. The resulting precipitate is separated by known procedures, e.g. by centrifuging or filtration. This precipitate contains the relaxin and is herein also referred to as relaxin-containing fraction.

Such relaxin-containing fraction can be used directly as a pharmaceutically active product. Since it is originating from a material which can be used as foodstuff, such fractions do not contain any harmful substances. Surprisingly this fraction is an excellent antacid, and it can be used as a remedy against gastric and intestinal disorders.

Pure relaxin is recovered from the precipitate, by suspending the precipitate in an aqueous buffer solution, using 0.5 to 5 times, preferably 0.5 to 2 times, of the pertaining volume. Still more preferred is a volume of 1:1. The pH of the buffer is of from 4.8 to 5.6. Preferred is a buffer of ammonium acetate having a pH of 5.3. However, customary phosphate buffers having a pH of from 4.6 to 6.2, can be used as well.

The resulting reaction mixture is filtered as required and 0.1 to 0.5% of sodium azide and 0.05 to 5 mM phenyl methane sulfonyl fluoride, or chloride, are added, as required.

The relaxin is now contained in the solution. The reaction mixture is filtered, as required, by means of membrane ultra-filtration (ultra-membrane filter) with the filter having an exclusion limit of 10,000 to 100,000 Daltons, preferably 50,000 Daltons. Such filters include, for example, Amicon filters or those made by Firma Berghof.

The resulting liquid can be concentrated, as required, at this point. In accordance with steps 10, 11 and 12, the reaction mixture, or a fraction containing relaxin, respectively, is filtered by means ultra-membrane or membrane ultra-filtration, or/and subjected to an ion-exchange chromatography, and/or a gel filtration. These steps may be carried out as often as desired whereby not all steps have to be carried out. However, gel filtration will be necessary in all instances.

Chromatography of relaxin-containing residues is known per se, and the known techniques can be used. For example, the solution or liquid can be treated in a carboxymethyl cellulose column (CMC) which was calibrated using a buffer solution. After the introduction period washing is carried out with buffer and the protein is eluted with a linear salt-gradient. The purification is carried out as described in the references indicated above. The resulting product is a specimen in which relaxin is present in concentrate form together with other proteins. This specimen can be dissolved again in buffer solution, as indicated above, and chromatography can be carried out as well as lyophilization. Purification is carried out, for example, in a column of Sephadex-G, using ammonium acetate buffer to elute. After several chromatographic purifications there is obtained a relaxin-containing specimen which is used for various tests and which contains relaxin of very high purity.

The gel filtration can also be carried out as high-pressure gel filtration. As gels one can use Sephadex, P-Gels of the Firma Bio Rad, or comparable gels (for example, PG-Gel), TSK-Gel of Merck, and others. When employing an ion-exchange chromatography one can use, as is indicated above, carboxymethyl cellulose, divinylbenzol-linked styrene sulfonic acid resins and the like.

As indicated above, it also an object of the invention to provide a process of preparing very pure relaxin in which relaxin is subjected to the step of ultra-purification by carrying out reversed-phase chromatography, HPLC-ion-exchange chromatography, HPLC-gel chromatography, batchprocessing by means of ion-exchange chromatography with subsequent eluting, and, as required, gel chromatography, as well as the step of concentrating the relaxin-containing fraction. The aforementioned steps of ultra-purification may be repeated as desired and in any desired sequence. It will also not be necessary to carry out all of these procedures.

The high-pressure or middle-pressure chromatography is preferably carried out using ion-exchange resins or 'reversed-phase' materials ($C_{18}$, $C_6$, $C_2$). When subjecting relaxin to such high-pressure or middle-pressure chromatography, which relaxin was considered pure in the past, there are obtained three peaks, one of which is pharmacologically effective. On the other hand, when subjecting a relaxin having its origin in human placenta, in high-pressure or low-pressure chromatography to a separation including separating it in a carboxymethyl cellulose column, there are obtained four peaks, as is indicated in FIG. 1, and one of these peaks is pharmacologically effective.

The preparative separation of, or purification to obtain an ultra-pure, relaxin is carried out with high-pressure or middle-pressure chromatography systems which are particularly designed for the ion-exchange chromatography of peptides and proteins with a cation-exchanger [W. Voelter, H. Bauer, S. Fuchs and E. Pietrzik: *J. Chromatogr.* 153, 433–442 (1978); compare also W. Voelter "High Performance Liquid Chromatography in Peptide Research" in the Monography: High Performance Liquid Chromatography in Protein and Peptide Chemistry, Walter de Gruyter, Berlin, New York, 1981].

The disclosure in these references is expressis verbis referenced in this specification.

For eluting relaxin there is, for example, used a five-step concentration, and pH, gradient of pyridine acetate buffer. This is effective over a concentration range of 0.05 to 3 M pyridine and a pH range of 3.0 to 6. In reversed-phase chromatography an acetonitrile-gradient has been found to be particularly useful, among others. Approximately 4% of the eluate were subjected, for detection, to a continuous partial hydrolysis in 6N sodium hydroxide solution, and resulting free amino groups are detected photometrically by means of an acidic ninhydrin reagent at 570 nm. This procedure allows the determination of peptides without free amino groups, as well as larger peptides having a greater sensitivity. The detection limit is below 1 μg per fraction.

The isolated fractions are directly recovered as salt-free products by lyophilizing, because pyridine acetate buffer can be evaporated without leaving a residue.

When separating relaxin using a strongly acidic ion-exchanger on the basis of a crosslinked polystyrene divinylbenzol lattice, several fractions are obtained. Fractions obtained by means of the middle-pressure system are concentrated under vacuum, introduced into double-distilled water, and lyophilized.

Further embodiments of the invention and other inventive features are contained in the claims.

DESCRIPTION OF THE DRAWING

In the drawing, which illustrates that which is presently regarded as the best mode of carrying out the invention.

Figure 1:
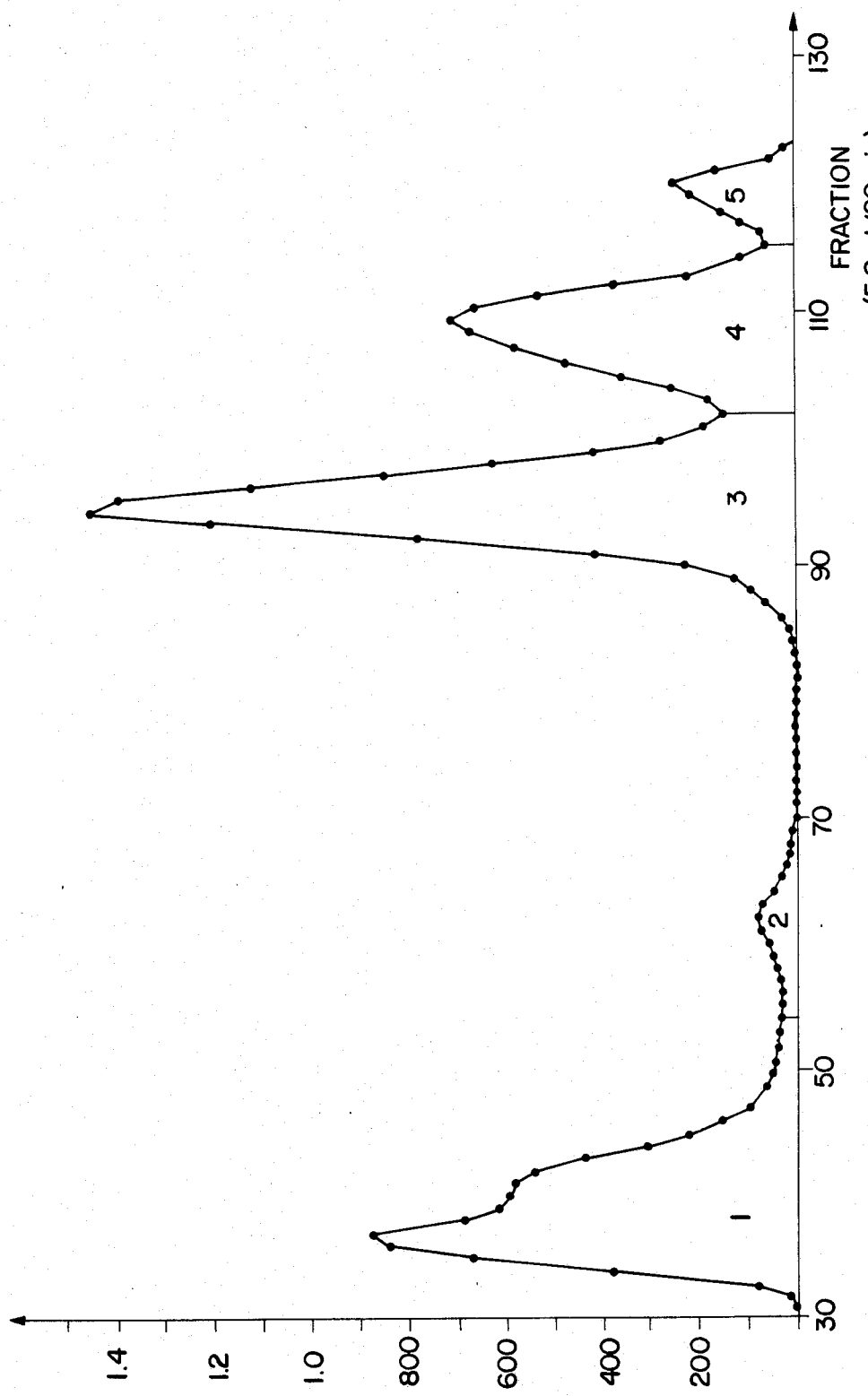
FIG. 1 is indicative of gel filtration of the raw relaxin-fraction extracted from human placenta.

The following detailed description of the single figure in the drawing as well as the following examples serve to further illustrate the invention.

FIG. 1—gel filtration of the raw relaxin-fraction extracted from human placenta by means of a Sephadex-G-50 column (2.6×100 cm). Equilibration and eluting were carried out using 0.2 M ammonium acetate (pH 6.8, 0.2% $NaN_3$). The flow rate was 15 ml/h. Fractions were collected every 15 min., and detection was again at 280 nm.

For the determination or analysis of relaxin there were used the known test methods, such as radioimmunoassay or a 'bio-test'. The 'bio-test' is carried out in accordance with the method suggested by Steinitz et al.: *Endocrinol.* 67, 102, 1966; while RIA is carried out as described by E. Loumaye, B. Teuwissen and K. Thomas, *Gynecol. Obstet. Invest.*, 9, pp. 262–267, 1978.

EXAMPLE I (a) Pre-purification of Relaxin

To approximately 2 l of fresh, cooled cow milk are added 600 mg $NaN_3$ and a small amount (full spatula tip) of phenyl methane sulfonyl fluoride. Next are slowly added, while stirring with a magnetic stirrer, 375 ml of concentrated, fuming HCl. On addition of the hydrochloric acid the milk becomes more viscous, and a flocculent, white substance separates. Stirring is continued for a further 15 minutes, cooling at +4° C. for 24 hours.

Precipitated casein is next separated by filtration or suction-filtration. A yellow liquid having a volume of approximately 2.4 l is obtained. The resulting filtrate is cooled for 3 hours at +4° C. Then there is added 1.8 l acetone which was cooled for 3 hours at +4° C. The solution is held at +4° C. for 12 hours.

Proteins which are insoluble in this medium e.g. γ-globulines, precipitate. These precipitated proteins are separated from the solution by filtration. There is then obtained a light-yellow liquid of a volume of about 3.2 l. To this are added a 5-fold volume, i.e. 16 l, of acetone which has been cooled for 3 hours at −60° C. An immediate flocculation of a white precipitate is observed. The solution is left at +4° C. for about 12 hours. The precipitate is then filtered and dried over $CaCl_2$ in a vacuumdesiccator. This procedure yields about 60 g of dry substance which comprises raw relaxin.

(b) Purification of Raw Relaxin

The dry substance is dissolved in 100 ml of a 50 mMol ammonium acetate buffer, at a pH of 5.3 and also containing 0.02% $NaN_3$. The supernatant solution is centrifuged for 20 minutes at 400 rpm, or filtered. This yields approximately 80 ml which may require further filtration for fully clearing it.

This solution is introduced, at a rate of approximately 25 ml/h, into a carboxymethyl cellulose column (CM-52, 2.6×40 cm). Prior to this, the column is equilibrated with 50 mMol $NH_4OOCCH_3$ buffer, at pH 5–7, also containing 0.02% $NaN_3$. After feeding for approximately 3 hours (also with reservoir and adapter), washing is carried out 2 or 3 times, each with 1 ml buffer solution, and protein is eluted using a linear salt-gradient. The linear salt-gradient is produced by means of a gradient-mixer, which contains, in the receiving-vessel, 1300 ml of 0.1 Mol NaCl (or also of from 0 to 0.4 M NaCl) dissolved in the above buffer solution, and in the receiving-vessel, 2300 ml of 0.5 Mol NaCl, dissolved in the above buffer solution. Any protein which is not absorbed is washed from the column using 0.1 Mol NaCl solution, or pure buffer. Relaxin is only eluted from the column at an NaCl concentration of approximately 0.25 to 0.45 Mol/l NaCl. Using a fractionator, a new fraction is collected in time-controlled manner every 15 minutes. The relaxin-containing fractions, which are detected photometrically at 280 nm, are collected in peakwise manner and are lyophilized.

Lyophilized protein is dissolved in a small amount of Ampuwa ® which also contains 0.02% NaN₃. There is obtained a yellow liquid of a volume of about 3 to 5 ml. This may contain residues or impurities which have to be removed by filtration using a white-band-filter. In order to de-salt this solution, it is introduced into a Sephadex-G-10 column (1.5×75 cm; or, alternatively, a P-GDG, or P-2 column, 5 to 6 ml/15 min. fraction). Chromatography is carried out at full speed, and approximately 10 ml per fraction are obtained at a fractionating time of 20 minutes. The individual fractions are measured photometrically at 280 nm, and the protein-containing fractions are collected and lyophilized.

Lyophilized and desalted protein, collected from 10 l of milk, is subsequently in a small amount of 0.2 Mol ammonium acetate buffer also containing 0.02% NaN₃. There is obtained a yellow liquid, 5 to 10 ml, which is to be clarified by filtration or centrifuging. This solution is treated in a Sephadex-G-50 - (super)fine column (100×2.6 cm) which had been equilibrated with 0.2 Mol NH₄OOCCH₃/0.02 NaN₃. The flow rate is adjusted to 4 to 6 ml per 20 minutes. A new fraction is collected every 20 minutes with the fractionating equipment. The relaxin-containing fractions are detected photometrically at 280 nm, collected in peakwise manner and lyophilized.

EXAMPLE II

Regular decaseined milk powder, 1000 g, is suspended in 10 l of water. The suspension is cooled in the ice-box at +4° C. in a closed container.

Treatment is continued on 10 l as described in Example I(b) above. The product is a relaxin-containing fraction in the form of a white powder.

Determination of the Relaxin

The determination of relaxin is carried out by radio-immunoassay (RIA), or by the 'bio-test', see the above references.

Execution of the Radioimmunoassay

For iodizing, 5 μg relaxin, dissolved in 10 μl of 0.1 M borate buffer (pH 8.5), are added to 4 mCi of Bolton-Hunter reagent and shaken for 15 minutes at 0° C. There is added 0.5 ml of a 0.2 M glycine solution in 0.1 M borate buffer and shaking atain at 0° C. for 5 minutes. The separation of relaxin is carried out by gel chromatography using a Sephadex-G-25 column (25×1 cm), with 0.05 M phosphate buffer (pH 7.5). The fractions containing radioactivily marked relaxin are diluted with 0.5 ml of a buffer solution PM 16 with 5% ovalbumin and used as stock solution for the assay. For the standard curve there are added, respectively, 100 μl of the different standard solutions (156 to 20,000 pg relaxin per ml PM 16), as well as 300 μl of an SMA control serum and 100 μl PM 16 buffer solution. To this are added antibody diluent which is obtained as follows:

Antiserum R6 is diluted in the ratio 1:36,000 with EDTA buffer (0.05 M EDTA—Na₂ in PM 16 buffer adjusted to pH 7.2 with NaOH to which is added 1:60 rabbit serum). This is maintained for 1 h at +4° C. and then are added 100 μl tracer solution (stock solution of the iodized relaxin by dilution with PM 16: 1% ovalbumin to approximately 10,000 cpm/100 ml). Incubation is carried out for 24 h at +4° C. The precipitation of the antigen-antibody-complex is carried out in accordance with the double-antibody method with 200 μl rabbit globulin antibody 1:4, diluted with PM 16: 1% 200 μl ovalbumin. After 24 h at +4° C., centrifuging is carried out on 4000 g and after decanting measured in the gamma counter.

The non-specific binding is a dimension for determination of the interaction between antigen and non-specific antibodies, and is determined by addition of 100 μl of EDTA buffer to 300 μl control serum. Upon addition of 100 μl tracer solution one continues as described above.

The zero-binding is an expression of the binding between antigen and antibody, it is determined by the addition of 200 μl PM 16: 1% ovalbumin, 100 μl antiserum diluent, and 100% tracer solution, to 300 μl control serum.

Investigations have shown relaxin can be therapeutically utilized during different pathological conditions during pregnancies, such as premature delivery, impending miscarriage, and of the connecting-tissue (verbindungsgewebe). Relaxin, particularly relaxin of human origin, is of utmost importance for preparation of homologous radio-immunoassay apparatus for the determination of relaxin in human body fluids and tissues.

It was surprisingly also found now that relaxin retards or inhibits the formation of gastric fluid-secretion and prevents excess acidity in the stomach. This applies in particular to relaxin and relaxin-containing fractions which have been extracted from milk, particularly milk of cows.

Reference in this disclosure to details of the specific embodiments is not intended to restrict the scope of the appended claims, which themselves recite those features regarded as essential to the invention.

We claim:

1. A process for recoverying relaxin from decaseined mammalian milk which comprises adding to decaseined mammalian milk while maintaining it at a temperature of 1°-15° C., acetone in a ratio of 0.5-5.0/1.0, by volume, to precipitate protein from said decaseined milk without precipitating relaxin therefrom; separating precipitated protein from said decaseined milk while maintaining said temperature; adding to the resultant protein-free, decaseined milk acetone cooled to a temperature of about −10° to about −70° C. in a ratio of 1.0-10/1.0, by volume, to precipitate relaxin therefrom; maintaining said temperature for approximately 24 hours; separating precipitated relaxin from said protein-free, decaseined milk; suspending said precipitated relaxin in a 0.5-5 fold volume of an ammonium acetate buffer solution having a pH of 4.8-5.6; adding to said suspension 0.1-0.5% sodium azide; subjecting the resultant mixture to at least one of (a) ultra-membrane filtration and (b) ion exchange chromatography having an exclusion of 10,000-100,000 Daltons, in combination with gel filtration; and concentrating and recoverying a purified relaxin.

* * * * *